(12) United States Patent
Ganin

(10) Patent No.: US 6,914,958 B2
(45) Date of Patent: Jul. 5, 2005

(54) MULTI-PLANE ACQUISITION IN DIGITAL X-RAY RADIOGRAPHY

(75) Inventor: Alexander Ganin, Whitefish Bay, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 184 days.

(21) Appl. No.: 09/682,001

(22) Filed: Jul. 6, 2001

(65) Prior Publication Data

US 2003/0007594 A1 Jan. 9, 2003

(51) Int. Cl.[7] ................................................ H05G 1/60
(52) U.S. Cl. ...................................................... 378/26
(58) Field of Search .................. 378/21–27, 98.7–98.12

(56) References Cited

U.S. PATENT DOCUMENTS

| | | | | |
|---|---|---|---|---|
| 4,211,927 A | * | 7/1980 | Helstrom et al. | ............. 378/26 |
| 4,577,222 A | * | 3/1986 | Kruger et al. | ................ 378/22 |
| 4,602,378 A | | 7/1986 | Kelman et al. | |
| 4,996,413 A | | 2/1991 | McDaniel et al. | |
| 5,412,702 A | * | 5/1995 | Sata | ............................ 378/20 |
| 5,572,567 A | | 11/1996 | Khutoryansky et al. | |
| 5,636,259 A | | 6/1997 | Khutoryansky et al. | |
| 5,717,732 A | * | 2/1998 | Tam | ............................ 378/26 |
| 5,734,694 A | | 3/1998 | Khutoryansky et al. | |
| 5,751,783 A | | 5/1998 | Granfors et al. | |
| 5,751,788 A | | 5/1998 | Khutoryansky et al. | |
| 5,870,450 A | | 2/1999 | Khutoryansky et al. | |
| 5,930,328 A | | 7/1999 | Nakamura et al. | |
| 6,222,902 B1 | * | 4/2001 | Lin et al. | ...................... 378/22 |

* cited by examiner

Primary Examiner—Craig E. Church
(74) Attorney, Agent, or Firm—McAndrews, Held & Malloy, Ltd.; Peter J. Vogel; Michael A. Dellapenna

(57) ABSTRACT

A method is provided for acquiring digital x-ray images. Scan parameters designating slices of interest from a patient anatomy are identified. The travel distance and the speed of the x-ray tube and the detector are determined from the scan parameters. The patient is scanned in a first direction to obtain a first x-ray image utilizing a servo-tomo function based on the scan parameters. The image is saved in an image storage device and is displayed. The patient is scanned in a second direction to obtain a second x-ray image utilizing the servo-tomo function based on the scan parameters. The image is saved and displayed simultaneously with the first image in a multi-image format. After each scan, the operator may modify the scan parameters designating a slice of interest before initiating the next scan.

7 Claims, 4 Drawing Sheets

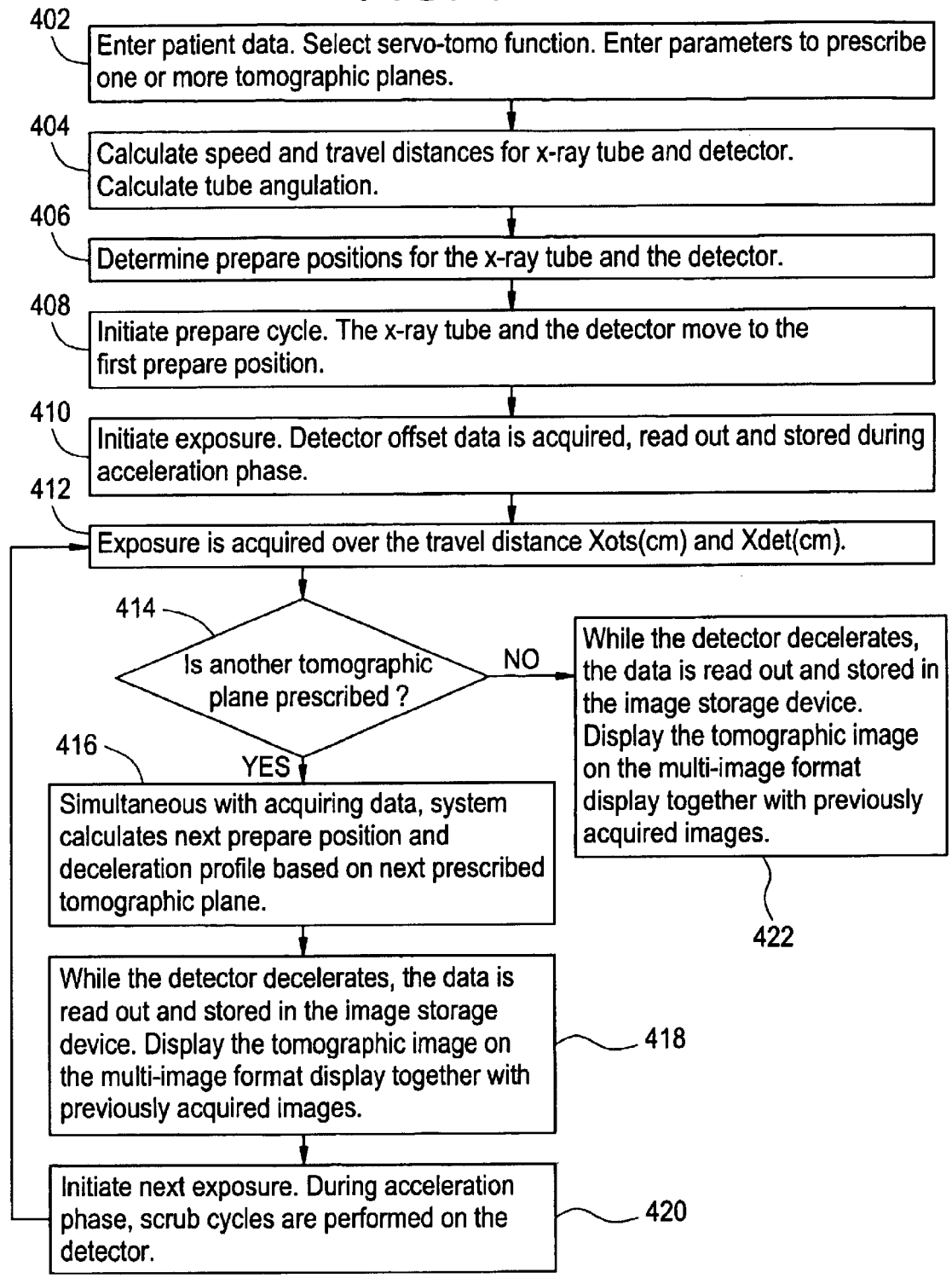

MULTI-PLANE ACQUISITION IN DIGITAL X-RAY RADIOGRAPHY

BACKGROUND OF INVENTION

An embodiment of the present invention relates to x-ray imaging systems. In particular, an embodiment of the present invention relates to multiple plane imaging in digital x-ray systems using the servo-tomo function.

Today, doctors and technicians commonly have access to very sophisticated medical diagnostic x-ray imaging devices. Typically, during the operation of an x-ray imaging device, an x-ray source emits x-ray photons under very controlled circumstances. The x-ray photons travel through a region of interest (ROI) of a patient under examination and impinge upon a detector. In the past, x-ray imaging devices employed film based or CR plate detectors. However, recent developments have led to solid state detectors comprised of a grid of discrete detector elements that individually respond to exposure by x-ray photons. One such detector is described in U.S. Pat. No. 4,996,413 to McDaniel et al. Regardless of the detector used, however, the goal remains the same, namely to produce a clear resultant image of the desired structures of interest within the ROI.

There is an inherent difficulty associated with producing a clear resultant image, however. In particular, because the x-ray photons travel through the entire patient, the image formed on the detector is a superposition of all of the anatomic structures through which x-ray photons pass, including the desired structures of interest. The superposition of anatomic structures is sometimes referred to as "anatomic noise". The effect of anatomic noise on the resultant image is to produce clutter, shadowing, and other obscuring effects that render the resultant image much less intelligible than the ideal clear resultant image.

One technique commonly utilized to produce a clear resultant image of the anatomy of interest is tomography. Tomography blurs the structure both above and below a tomographic plane that contains the desired structures of interest by moving both the x-ray tube and the detector during a single exposure. Several methods may be used to produce a tomographic image. Each method utilizes several parameters to identify the tomographic plane which must be specified by the x-ray technician. In linear tomography, the x-ray tube and the detector maintain the same relationship to each other. The x-ray tube and the detector may be mechanically fixed so that their relationship remains constant, or the x-ray tube and the detector may maintain a constant relationship by utilizing angulation to keep the x-ray tube aimed at the detector.

Another technique used by x-ray imaging devices involves a "servo-tomo" function. Systems operated in accordance with a servo-tomo function do not mechanically fix or maintain the same relationship between the x-ray tube and the detector. Instead, the servo-tomo function controls movement of the x-ray tube and the detector relative to one another, but such movement is not identical. The servo-tomo function allows the x-ray tube and the detector to move in opposite directions, similar to linear tomography, but also to move at different speeds and distances. Thus, the x-ray tube may move a larger distance at a faster speed compared to the distance and speed of the detector during the x-ray exposure. The servo-tomo function may be used to view anatomy such as joints and the liver, for example.

Typically, one tomographic plane of the anatomy of interest is not sufficient for medical diagnosis. Often a radiologist desires to see multiple tomographic planes, with each tomographic image focused on a different point in the patient's anatomy. The acquisition of successive tomographic planes is called multi-plane tomography.

Several disadvantages exist with the current use of multi-plane tomography. For example, for x-ray systems that utilize the servo-tomo function with a film based or CR plate detector (i.e. analog systems), the film or CR plate may need to be replaced with another film cassette or CR plate before additional tomographic images can be acquired. Also, the radiologist must wait for the images to be developed before evaluating the images. Additionally, one or more parameters used to define the tomographic plane need to be modified by the x-ray technician before the next tomographic image can be acquired. The foregoing steps result in increased time for the examination, thus resulting in a lower patient throughput and a lower utilization rate of the x-ray machine. The examination time may further increase if, once the film or CR plates are developed, it is determined that additional or different slice information is desired. It is also possible that unnecessary exposures may be taken because the images are not reviewed as they are acquired. Thus, a need has long existed in the industry for a method and apparatus for multi-plane acquisition that addresses the problems noted above and previously experienced.

SUMMARY OF INVENTION

In accordance with at least one embodiment, a method is provided to acquire digital x-ray images. Scan parameters designating slices of interest from a patient anatomy are identified. A scan of the patient is initiated in a first direction to obtain a first x-ray image and a scan is initiated in a second direction to obtain a second x-ray image. The scans utilize a servo-tomo function based on the scan parameters. The scan parameters may include at least one of a focal plane of interest, a sweep angle, a focal plane thickness and an exposure time. The scan parameters may be modified before scanning the next image. The detector and x-ray tube travel distances and sweep velocities are calculated based on the scan parameters and are loaded before each image is acquired.

In accordance with at least one embodiment, first and second preparation positions are calculated. The first and second preparation positions are located on opposite ends of a scan range over which the first and second scans of the patient are acquired. The first image is initiated beginning at a prepare position located at one end of the scan range, and the second image is initiated beginning at a prepare position located at the other end of the scan range. The first x-ray image is displayed after scanning in the first direction. The second x-ray image is displayed with the first image in a multi-image format after scanning in the second direction. The acquired images are stored in an image storage device.

In accordance with at least one embodiment, a method is provided for displaying digital x-ray images in a multi-image format. Scan parameters are identified to designate multiple slices of interest from a patient anatomy. The scan parameters include at least one of a focal plane of interest, a sweep angle, a focal plane thickness, and an exposure time. A series of images corresponding to the multiple slices of interest are acquired. The images are acquired utilizing a servo-tomo function and are saved in an image storage device. The images are displayed simultaneously as each of the images are acquired. After the acquisition and display of each image, the acquisition is halted until an operator starts the next acquisition.

In accordance with at least one embodiment, the scan parameters identifying a slice of interest not yet acquired may be changed. All of the scan parameters needed for acquisition of the images may be identified. The detector and x-ray tube travel distances and sweep velocities may be calculated based on the scan parameters. The x-ray tube angulation may be calculated based on the x-ray tube travel distance and the scan parameters. First and second preparation positions located on opposite ends of the scan range are calculated. The prepare position is loaded after each acquisition and is located at the opposite end of the scan range as the previous prepare position. The precalculated stored detector and x-ray tube velocity and travel distances are loaded before each acquisition. The patient is scanned in a first direction, then the patient is scanned in a direction opposite to the first direction.

BRIEF DESCRIPTION OF DRAWINGS

FIG. 4 illustrates a method to acquire multi-plane tomographic images utilizing the servo-tomo function in accordance with an embodiment of the present invention.

The foregoing summary, as well as the following detailed description of the embodiments of the present invention, will be better understood when read in conjunction with the appended drawings. It should be understood, however, that the present invention is not limited to the arrangements and instrumentality shown in the attached drawings.

DETAILED DESCRIPTION

Figure 1:
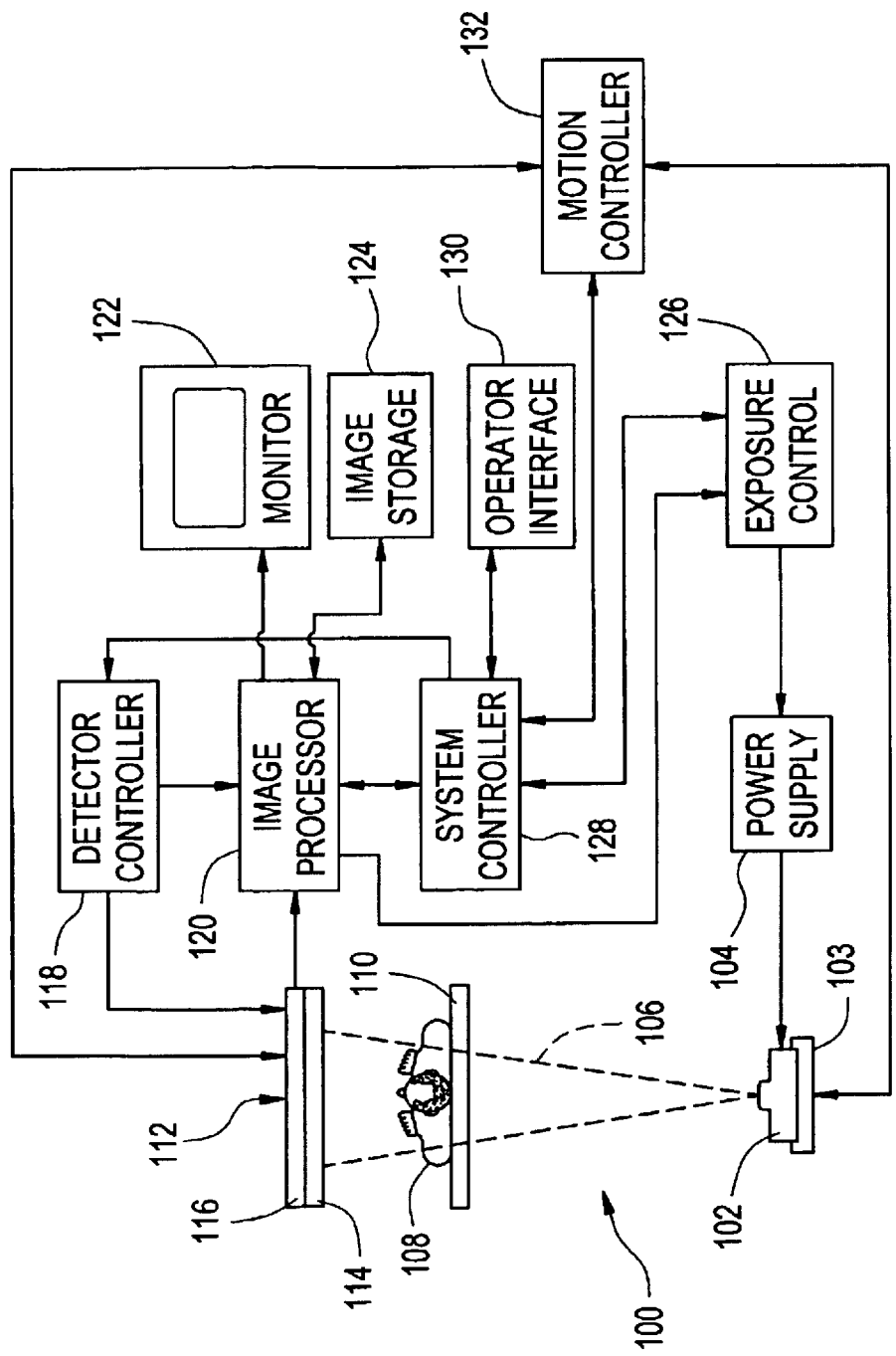
FIG. 1 illustrates an x-ray apparatus that operates in accordance with an embodiment of the present invention.

FIG. 1 illustrates an x-ray apparatus 100 that operates in accordance with an embodiment of the present invention. The x-ray apparatus 100 includes an x-ray tube 102 housed in an x-ray tube system 103. The x-ray tube 102 emits an x-ray beam 106 when excited by a power supply 104. As illustrated, the x-ray beam 106 is directed toward a patient 108 lying on an x-ray transmissive table 110. The portion of the beam 106 which is transmitted through the table 110 and the patient 108 impinges upon an x-ray detector 112. The X-ray detector 112 comprises a scintillator 114 that converts the x-ray photons to lower energy photons in the visible spectrum. Contiguous with the scintillator 114 is a photodetector array 16 which converts the light photons into an electrical signal. A detector controller 118 contains electronics for operating the detector array to acquire an image and to read out the signal from each photodetector element. During techniques such as servo-tomo, a motion controller 132 moves the x-ray tube 102, the x-ray tube system 103, and the x-ray detector 112 while the x-ray apparatus 100 acquires images. There may be one or more motion controller 132.

The output signal from the photodetector array 116 is coupled to an image processor 120 that includes circuitry for processing and enhancing the x-ray image signal. The processed image then is displayed on a video monitor 122 and may be archived in an image storage device 124. The image processor 120 additionally produces a brightness control signal which is applied to an exposure control circuit 126 to regulate the power supply 104 and thereby the x-ray exposure. The overall operation of the x-ray apparatus 100 is governed by a system controller 128 which receives commands from the x-ray technician (or other operator) via an operator interface panel 130. The x-ray apparatus 100 is known as a digital system, as the image information is acquired, saved and displayed without the use of a film based or CR plate detector.

Figure 2:
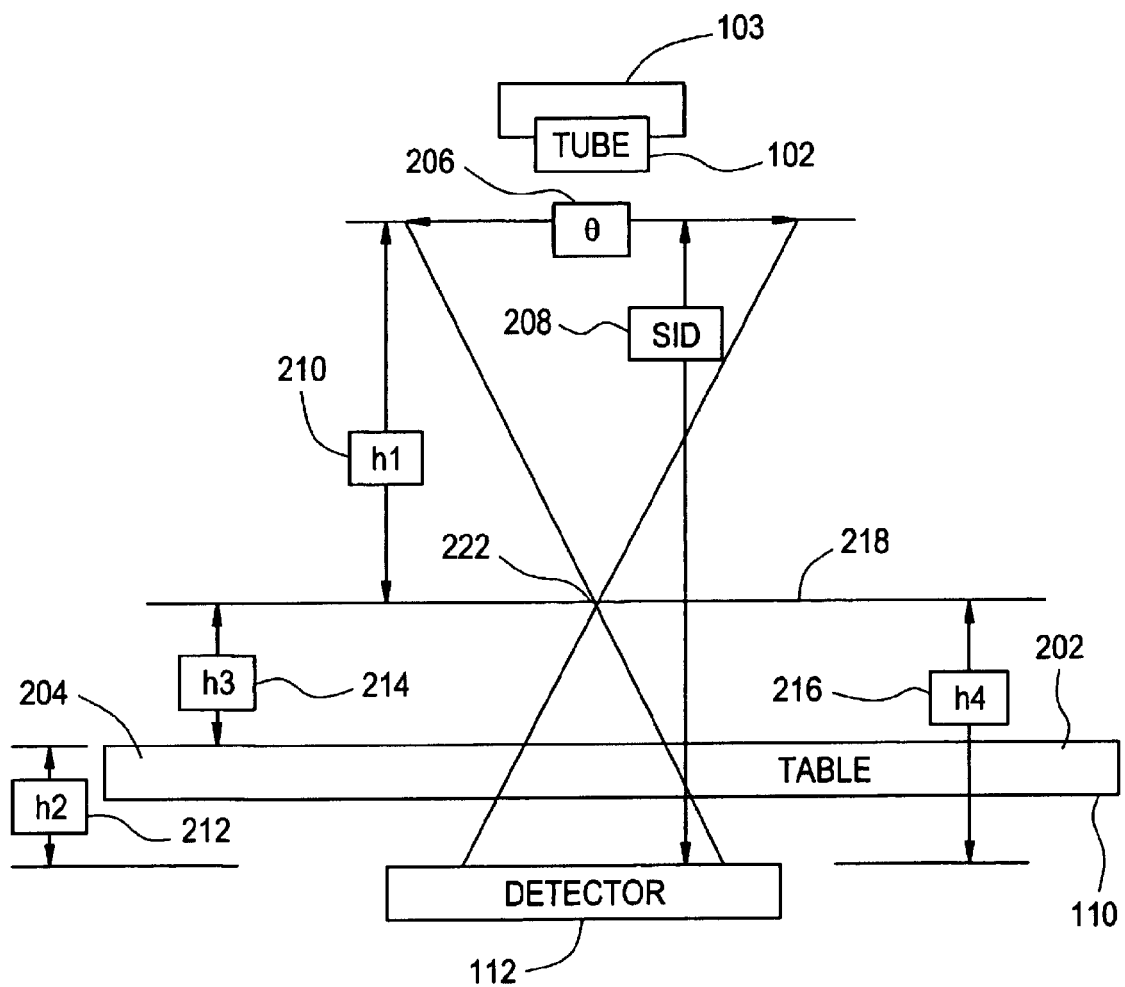
FIG. 2 graphically illustrates parameters as related to an x-ray apparatus that may be utilized to acquire an image of a tomographic plane in accordance with an embodiment of the present invention.

FIG. 2 graphically illustrates parameters as related to x-ray apparatus 100 that may be utilized to acquire an image of a tomographic plane in accordance with an embodiment of the present invention. FIG. 2 includes an x-ray tube 102, an x-ray tube system 103, a table 110, and a detector 112 as previously discussed. A patient (not shown) may lie on the table 110 with their head towards the head of the table 202 and their feet toward the foot of the table 204. The operational parameters include a sweep angle ($\theta$) 206, a source to image distance (SID) 208, a focal spot to fulcrum level distance (h1) 210, a detector to tabletop distance (h2) 212, a fulcrum plane (h3) 214, a detector to fulcrum level distance (h4) 216, a fulcrum level 218, and a fulcrum point 222.

The x-ray tube 102 and the detector 112 illustrated in FIG. 2 are not mechanically connected in a manner that they mirror movement of one another. Instead, the relationship between the x-ray tube 102 and the detector 112 is maintained by the system controller 128. Thus, when an exposure is taken utilizing the servo-tomo function, the motion controller 132 may move the x-ray tube 102 and the detector 112 at different speeds and distances. Additionally, the motion controller 132 may change the angle of the x-ray tube 102 relative to the detector 112 throughout the acquisition. For example, an x-ray technician enters information into the operator interface panel 130 to set up an x-ray exposure and acquire a tomographic image utilizing the servo-tomo function. The system controller 128 receives information from the operator interface panel 130. The system controller 128 utilizes the information to control the synchronous movement of the x-ray tube 102 and the detector 112 during the exposure.

The x-ray technician may enter into the operator interface panel 130 an exposure time, a fulcrum level 218, and either a sweep angle (θ) 206 or a thickness of the tomographic plane for each tomographic image. In addition, x-ray tube 102 exposure parameters, such as tube voltage and tube current may be entered. The remaining parameters illustrated in FIG. 2 are calculated or known by the system controller 128. One parameter that is entered by the x-ray technician is the fulcrum level 218. The fulcrum level 218 determines the position of the tomographic plane, which may also be called a focal plane or a tomographic slice, relative to the tabletop. The anatomy of interest is located within the tomographic plane, and the motion of the x-ray tube 102 and the detector 112 cause blurring of the anatomy above and below the tomographic plane. A different fulcrum level 218 may be entered for each tomographic image.

During the exposure, the motion controller 132 moves the x-ray tube 102, the x-ray tube system 103, and the detector 112. The motion of the x-ray tube system 103 and the detector 112 is linear, and the x-ray tube system 103 and the detector 112 move in opposite directions. For example, the x-ray tube system 103 may move towards the foot of the table 204 and the detector 112 may move towards the head of the table 202. The motion of the x-ray tube 102 is angular, and takes the form of an angular rotation about the fulcrum point 222. The angular rotation keeps the central x-ray beam 106 directed through the fulcrum point 222. The fulcrum point 222 is located on the fulcrum level 218, thus each tomographic plane will have a different fulcrum point 222. The fulcrum point 222 is defined by the system controller 128 based upon the speed and the distance traveled by the x-ray tube 102 and the detector 112 during the exposure. Another parameter that may be entered by the x-ray technician is the sweep angle (θ) 206. The sweep angle (θ) 206 is the angle over which the x-ray exposure takes place. The size of the sweep angle (θ) 206 determines the tomographic plane thickness, or the size of the slice. For example, a large angle will result in a relatively thin tomographic slice, while a small angle will result in a relatively thick tomographic slice.

Often, a radiologist desires to see multiple tomographic planes. During a kidney study, for example, the radiologist may want to view three or four different tomographic planes. When utilizing the servo-tomo function to acquire multiple tomographic planes, as in multi-plane tomography, the sweep angle (θ) 206 may be utilized, together with a predetermined look-up table, to determine the thickness of the tomographic plane. Then, once the thickness of the tomographic plane is known, along with the correlating fulcrum levels 218, one or more plane interval may be specified. The plane interval is the distance between each successive tomographic plane. Alternatively, the x-ray technician may determine the desired thickness of one or more tomographic planes. Based on the thickness of the plane, a predetermined look-up table is then utilized to determine the sweep angle (θ) 206 corresponding to each plane.

The parameters and calculations below are discussed in terms of centimeters (cm). However, the English units of measure may also be used.

The focal spot to fulcrum level distance (h1) 210 is the distance in cm from the focal spot of the x-ray tube 102 to the fulcrum level 218. The source to image distance (SID) 208 is the distance in cm from the focal spot of the x-ray tube 102 to the detector 112. In one example, the source to image distance (SID) 208 is 101 cm. The detector to tabletop distance (h2) 212 is the distance in cm from the tabletop to the detector 112. For instance, the detector to tabletop (h2) 212 distance may be 7 cm. The fulcrum plane (h3) 214 is the distance in cm from the fulcrum level 218 to the tabletop. By way of example, the fulcrum plane (h3) 214 can be from 0 cm to 25 cm in width. The detector to fulcrum level distance (h4) 216 is the distance in cm from the fulcrum level 218 to the detector 112. Using the above information, the following relationships between SID, h1, h2, h3, and h4 can be represented as follows:

$$h1 = SID - (h2 + h3), \text{ and}$$

$$h4 = h2 + h3.$$

In order to acquire a tomographic image utilizing the servo-tomo function, a travel distance (or scan range) and a sweep velocity are calculated for both the x-ray tube 102 and the detector 112. The travel distance is the distance the x-ray tube 102 or the detector 112 moves during the exposure. The sweep velocity is the speed the x-ray tube 102 or the detector 112 moves to cover the travel distance in a specified amount of time. The travel distance and the sweep velocity of the x-ray tube 102 may not be the same as the travel distance and the sweep velocity of the detector 112. The following equation is utilized to calculate the distance in cm that the x-ray tube 102 will travel during the exposure:

$$Xot(\text{cm}) = 2 \times h1 \times \tan(\theta/2), \quad \text{Equation 1}$$

where Xot is the distance that the overhead tube (i.e. the x-ray tube 102) travels in cm, h1 is the focal spot to fulcrum level distance (h1) 210 and θ is the sweep angle (θ) 206. The sweep velocity for the x-ray tube 102 can be calculated as follows:

$$Vot(\text{cm/s}) = Xot(\text{cm})/t(s), \quad \text{Equation 2}$$

where Vot(cm/s) is the speed of the overhead tube (i.e. the x-ray tube 102) in cm per second, Xot(cm) is the result of Equation 1, and t(s) is the exposure time in seconds entered by the x-ray technician. By way of example, the exposure time may be within the range of 0.5 seconds to 2 seconds. The following equation is utilized to calculate the distance in cm that the detector 112 will travel during the exposure:

$$Xdet(\text{cm}) = 2 \times h4 \times \tan(\theta/2), \quad \text{Equation 3}$$

where Xdet(cm) is the distance the detector 112 travels in cm, h4 is the detector to fulcrum level distance (h4) 216, and θ θ is the sweep angle (θ) 206. The sweep velocity for the detector 112 can be calculated as follows:

$$Vdet(\text{cm/s}) = Xdet(\text{cm})/t(s), \quad \text{Equation 4}$$

Where Vdet(cm/s) is the speed of the detector 112 in cm per second, Xdet(cm) is the result of Equation 3, and t(s) is the exposure time in seconds entered by the x-ray technician.

Once the travel distance Xot(cm) and sweep velocity Vot(cm/s) have been calculated for the x-ray tube 102, the angulation of the x-ray tube 102 throughout the scan can be determined. The angle of the x-ray tube 102 is zero degrees when the x-ray beam 106 strikes the detector 112 at a 90 degree angle. In other words, the x-ray tube 102 is in a vertical position. The angle of the x-ray tube 102 is measured from the zero degrees position. During an exposure, the position at which the x-ray tube 102 is at zero degrees corresponds with the distance and time at which the detector has completed one half of its travel distance Xot(cm) and one half of its travel time t(s). The following equation is used to determine the angle of the x-ray tube 102:

$$Aot(deg) = 2 \times arctan(Xotp(cm) \times Totp(s)/2 \times h1), \quad \text{Equation 5}$$

Where Aot(deg) is the angle in degrees of the x-ray tube 102 during the x-ray tube system 103 linear motion, Xotp(cm) is the distance in cm from the point at which the angle of the x-ray tube 102 is zero (i.e. when the scan is one half complete), Totp(s) is the time in seconds the x-ray tube 102 is away from the point at which the angle of the x-ray tube 102 is zero, and h1 is the focal spot to fulcrum level distance (h1) 210.

For example, the distance measured from the zero degrees position towards the head of the table 202 is a negative number (−Xotp(cm)), and the distance measured from the zero degrees position towards the foot of the table 204 is a positive number. Thus, if the x-ray tube 102 starts its travel at the head of the table 202 and moves towards the foot of the table 204, the x-ray tube 102 will be moved through a negative angle that is continuously decreased until the sweep is one half completed. Then, the x-ray tube 102 will be moved through a positive angle that is continuously increased for the second half of the sweep.

The following examples utilize various imaging parameters in Equations 1 through 5 to define Images 1 through 4. For all examples, the detector to tabletop distance (h2) 212 is 7 cm and the source to image distance (SID) 208 is 101 cm. Table 1 lists the speed and travel distances for the x-ray tube 102 and the detector 112 for Images 1 and 2, and Table 3 lists the speed and travel distances for the x-ray tube 102 and the detector 112 for Images 3 and 4. Table 2 lists the angulation for the x-ray tube 102 at several positions for Images 1 and 2, and Table 4 lists the angulation for the ray tube 102 at several positions for Images 3 and 4.

The x-ray technician enters the fulcrum plane (h3) 214, the sweep angle (θ) 206, and the exposure time in seconds (t(s)) for Image 1 and Image 2. In Table 1, the fulcrum plane (h3) 214 of Images 1 and 2 is 0, and thus the tomographic plane (slice) is next to the tabletop. Image 1 has a sweep angle (θ) 206 of 8 degrees and Image 2 has a sweep angle (θ) 206 of 40 degrees. As stated above, a small sweep angle (θ) 206 will result in a thicker tomographic slice and a larger sweep angle (θ) 206 will result in a thinner tomographic slice. Thus, Image 1 will result in a thicker tomographic slice than Image 2. For example, the exposure time of Image 1 may be .5 seconds, and the exposure time of Image 2 may be 2 seconds. The system controller 128 utilizes Equations 1 through 4 to calculate the speed and travel distances for the x-ray tube 102 and the detector 112 as illustrated in Table 1::

TABLE 1

| Image | Fulcrum Plane (h3) (cm) | Sec (s) | θ | Xot(cm) | Vot(cm/s) | Xdet(cm) | Vdet(cm/s) |
|---|---|---|---|---|---|---|---|
| 1 | 0 | .5 | 8 | 13.1 | 26.3 | 1 | 2 |
| 2 | 0 | 2 | 40 | 68.4 | 34.2 | 5.1 | 2.55 |

The system controller 128 then utilizes Equation 5 and the parameters from Table 1 to calculate the angle of the x-ray tube 102 as it moves through the sweep angle (θ) 206. Table 2 lists several values for the angle of the x-ray tube Aot(deg) as the x-ray tube 102 moves from the head of the table 202 to the foot of the table 204:

TABLE 2

| Image | Xotp(cm) | Totp(s) | Scan ¼ complete Aot(deg) | Scan complete Aot(deg) |
|---|---|---|---|---|
| 1 | −3.275 | .125 | −.25 | N/A |
| 1 | 6.55 | .25 | N/A | 1 |
| 2 | −17.1 | .5 | −5.21 | N/A |
| 2 | 34.2 | 1 | N/A | 20.62 |

Continuing the above example, the x-ray technician enters the fulcrum plane (h3) 214, the sweep angle (θ) 206, and the exposure time in seconds for Image 3 and Image 4. In Table 3, the fulcrum plane (h3) 214 of Image 3 and 4 is 25 cm, thus the tomographic slice is located at the furthest available position from the tabletop. The sweep angle (θ) 206 and exposure time of Image 3 is the same as that of Image 1, and the sweep angle (θ) 206 and exposure time of Image 4 is the same as that of Image 2. Once again, the system controller 128 utilizes Equations 1 through 4 to calculate the speed and travel distances for the x-ray tube 102 and the detector 112 as illustrated in Table 3:

TABLE 3

| Image | Fulcrum Plane (h3) (cm) | Sec (s) | θ | Xot(cm) | Vot(cm/s) | Xdet(cm) | Vdet(cm/s) |
|---|---|---|---|---|---|---|---|
| 3 | 25 | .5 | 8 | 9.6 | 19.3 | 4.5 | 9 |
| 4 | 25 | 2 | 40 | 50.2 | 25.1 | 23.3 | 11.7 |

The system controller 128 utilizes Equation 5 and the parameters from Table 3 to calculate the angle of the x-ray tube 102 as it moves through the sweep angle (θ) 206. Table 4 lists several values for the angle of the x-ray tube Aot(deg) as the x-ray tube 102 moves from the head of the table 202 to the foot of the table 2044

TABLE 4

| Image | Xotp(cm) | Totp(s) | Scan ¼ complete Aot(deg) | Scan ½ complete Aot(deg) |
|---|---|---|---|---|
| 3 | −2.4 | .125 | −.249 | N/A |
| 3 | 4.8 | .25 | N/A | .996 |
| 4 | −12.55 | .5 | −5.21 | N/A |
| 4 | 25.1 | 1 | N/A | 20.6 |

Figure 3:
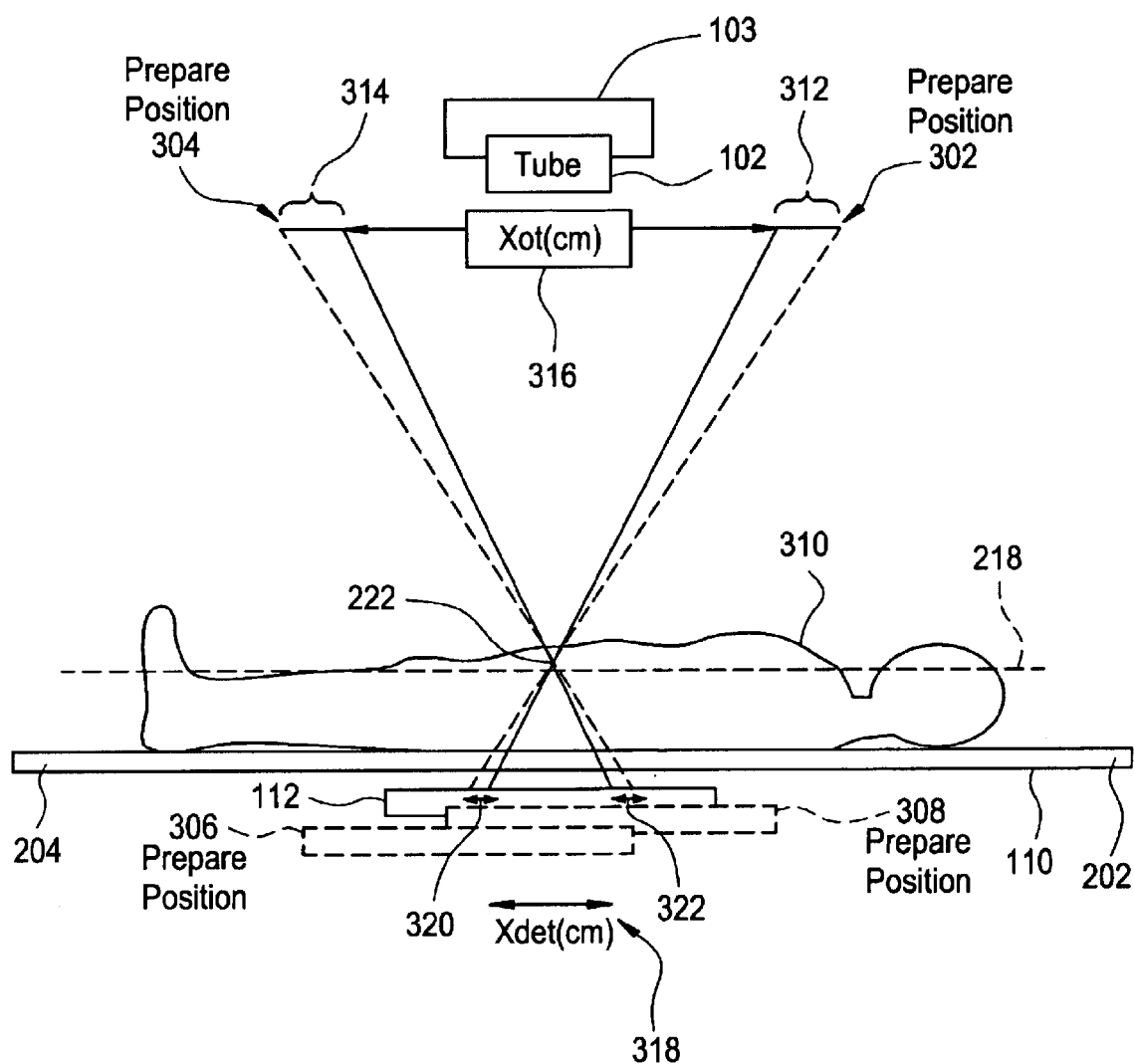
FIG. 3 illustrates positions of the x-ray tube and the detector of an x-ray apparatus utilized to acquire multiple servo-tomo images in accordance with an embodiment of the present invention.

FIG. 3 illustrates positions of the x-ray tube 102 and the detector 112 of an x-ray apparatus 100 utilized to acquire multiple servo-tomo images. FIG. 3 includes an x-ray tube 102, x-ray tube system 103, an x-ray transmissive table 110, a detector 112, a head of the table 202, a foot of the table 204, and a fulcrum point 222 as discussed previously. FIG. 3 further illustrates x-ray tube prepare positions 302 and 304, detector prepare positions 306 and 308, a patient 310, x-ray tube acceleration/deceleration phases 312 and 314, detector acceleration/deceleration phases 320 and 322, an x-ray tube travel distance (Xot(cm)) 316, and a detector travel distance (Xdet(cm)) 318.

FIG. 4 illustrates a method to acquire multi-plane tomographic images utilizing the servo-tomo function. FIGS. 3 and 4 will be discussed at the same time.

The patient 310 is positioned on the table 110 such that the patient's head is towards the head of the table 202, and the patient's feet are towards the foot of the table 204. The patient's 310 position will be determined by the anatomy that is being imaged.

At Step 402 of FIG. 4, the x-ray technician enters the patient data, such as name, anatomy being imaged, and the like, into the operator interface panel 130. The x-ray technician then selects an application (e.g., liver, kidney, heart, etc.) to acquire data utilizing the servo-tomo function, and enters the values for a set of parameters prescribing one or more tomographic planes. The parameters may be exposure time, sweep angle (θ) 206 or thickness of the tomographic plane, and fulcrum level 218 for each tomographic plane, as described previously. Any number of tomographic planes can be prescribed. The tomographic planes may be the same thickness, or may each have a different thickness.

For example, the x-ray technician may set up a study to image the liver of the patient 310. The x-ray technician enters the patient data into the operator interface panel 130 and selects an appropriate application utilizing the servo-tomo function, by which three tomographic images are acquired. The first image has a fulcrum level 218 at 5 cm from the tabletop and is 5 mm thick. The second image has a fulcrum level 218 at 8 cm from the tabletop and is 10 mm thick. The third image has a fulcrum level 218 at 11 cm from the tabletop and is 10 mm thick. The x-ray technician also enters how long each exposure will be in seconds. From these parameters, the system controller 128 determines the sweep angle (θ) 206 and a fulcrum point 222 for both the x-ray tube 102 and the detector 112 for each of the three scans.

At Step 404, the system controller 128 utilizes Equations 1 through 4 to calculate the speed and the travel distance for the x-ray tube 102 and the detector 112, and the x-ray tube 102 angulation, for each of the three scans. The sweep angle (θ) 206, the fulcrum point 222, the speed, the travel distance, and the x-ray tube 102 angulation may be different for each of the three scans. The speed, travel distances, and angulation may be stored, such as in Tables 1 through 4.

At Step 406, the system controller 128 uses the parameters entered by the x-ray technician and the speed and distance parameters calculated by the system controller 128 to calculate a prepare position 302 for the x-ray tube 102 and a prepare position 306 for the detector 112. The x-ray apparatus 100 utilizes motion controller 132 to move the x-ray tube 102, the x-ray tube system 103, and the detector 112 to and between the prepare positions 302, 304, 306 and 308. The locations of the prepare positions 302, 304, 306, and 308 are dependent upon the capabilities of the motion controller 132 to achieve and maintain a desired speed. The acceleration/deceleration phases 312 and 314 are the distances required for the x-ray tube 102 to accelerate and achieve the required speed for the exposure. The acceleration/deceleration phases 320 and 322 are the distances required for the detector 112 to accelerate and achieve the required speed for the exposure.

Continuing with the above example, the system controller 128 calculates at Step 406 that the x-ray tube 102 will require 10 cm of travel distance to achieve the speed calculated for the first image in Equation 2. The system controller 128 identifies the prepare position 302 as 10 cm from the beginning of the travel distance Xot(cm) 316, or 10 cm from the exposure start position in the direction of the head of the table 202.

At Step 408, the x-ray technician initiates the prepare cycle of the application. During the prepare cycle, the x-ray tube 102, the x-ray tube system 103, and the detector 112 move to the first identified prepare positions. For example, the x-ray tube 102 moves to the prepare position 302 identified for the first image acquisition, and the detector 112 moves to the prepare position 306 identified for the first image acquisition. The x-ray tube 102 will be angled according to the value calculated by Equation 5.

At Step 410, the first image exposure is initiated by the x-ray technician. The system controller 128 controls the simultaneous movement of the x-ray tube 102 and the detector 112. The x-ray tube 102 moves from the prepare position 302 in the direction of the foot of the table 204. The detector 112 moves from the prepare position 306 in the direction of the head of the table 202. While the detector 112 is accelerating through the acceleration/deceleration phase 320, the offset data of the detector 112 is acquired, read out and stored.

Next, at Step 412, the x-ray tube 102 has reached the start of the x-ray tube travel distance Xot(cm) 316, is moving at the speed calculated by Equation 2 (Vot (cm/s)), and begins to emit the x-ray beam 106. At the same time, the detector 112 has reached the start of the detector travel distance Xdet(cm) 318, is moving at the speed calculated by Equation 4 (Vdet(cm/s)), and begins to detect the x-ray beam 106. For anatomies of interest that lie in the tomographic plane (i.e. the focal plane), the x-ray beam 106 that transmits through a particular point in the patient 310 will be detected by the detector 112 at the same (x,y) location on the detector 112 for the duration of the scan because the x-ray tube 102 is angled to direct the x-ray beam 106 through focal spot 222 throughout the scan. For anatomies that lie outside the focal plane, however, the x-ray beam 106 that transmits through a particular point in the patient 310 will be detected at various (x,y) locations for the duration of the scan. For example, if the patient's liver is located within the focal plane, and a specific point in the patient's liver was detected at pixel location (100,100) at the beginning of the exposure, the specific point in the patient's liver will be detected at pixel location (100,100) for the entire exposure. Thus, the patient's liver which is located within the focal plane will be in focus and the anatomy not in the focal plane will be blurred.

At Step 414, while the image of Step 412 is being acquired, the system controller 128 determines whether another tomographic image is to be acquired. If another image is defined, the control passes to Step 416. If another image is not defined, the control passes to Step 422.

Continuing with the example above, another tomographic image is to be acquired, so the method continues to Step 416. At Step 416, the image of Step 412 is still being acquired. The x-ray tube 102 and the detector 112 have not yet completed their respective travel distances Xot(cm) 316 and Xdet(cm) 318. The system controller 128 calculates the deceleration profiles and the next prepare positions 304 and 308 for the x-ray tube 102 and the detector 112 based upon the parameters entered for the next image. The system controller 128 also utilizes the parameters entered for the second scan to calculate the speed and travel distance of the x-ray tube 102 and the detector 112, and the angulation of x-ray tube 102 according to the Equations 1 through 5.

At Step 418, the x-ray tube 102 and the detector 112 have completed their respective travel distances Xot(cm) 316 and Xdet(cm) 318. The x-ray tube 102 stops emitting x-rays, decelerates according to the deceleration profile, and stops moving. While the detector 112 is decelerating, the raw data acquired by detector 112 is read out by the image processor 120. The image processor 120 may correct the raw data by applying a gain map, pixel map, or the like before storing the data in the image storage device 124. The image is immediately displayed on the monitor 122 in a multi-image format display pattern. At the same time, the system controller directs the x-ray tube 102 to move to prepare position 304, and the detector 112 to move to prepare position 308. The x-ray apparatus 100 is now ready to acquire the second image.

Continuing the above example, the first acquired image is viewed on the monitor 122 and may be immediately evaluated. This is an advantage over the previous methods of acquiring servo-tomo images, as the image has to first be developed if film or a CR plate was used. Also, the image is stored in the image storage device 124, and can be further processed or reviewed at another time. Storing the image in the image storage device 124 provides an advantage over fluoroscopy, which is another method of imaging patient anatomy. In fluoroscopy, the images are viewed on the monitor 122 as they are acquired, but the images are not saved for future evaluation or processing.

An additional advantage is that the study can be terminated or modified, for example, if it is determined that the patient positioning may be improved or if different parameters are desired. By stopping the application before all the images are acquired, time is not wasted on acquiring images that do not show the desired anatomy, and thus the patient may be exposed to less radiation.

Another advantage of the method of FIG. 4 is that previously, only the parameters for one image were entered at a time. Once the image was acquired, then the second image would be set up. Also, the x-ray tube 102 and the detector 112 typically return to their first prepare positions 302 and 306. With the method of FIG. 4, the system utilizes prepare positions 304 and 308, eliminating the need to move the x-ray tube 102 and the detector 112 to their original starting positions. Additionally, because the parameters for all of the tomographic images are already entered, the next exposure can quickly be initiated. Using the method of FIG. 4 may shorten the time the patient must spend on the table and increase patient throughput.

At Step 420, the image exposure is initiated by the x-ray technician. The system controller 128 controls the simultaneous movement of the x-ray tube 102 and the detector 112. The x-ray tube 102 moves from the prepare position 304 in the direction towards the head of the table 202. The detector 112 moves from the prepare position 308 in the direction towards the foot of the table 204. The detector 112 performs a number of scrub cycles during the acceleration/deceleration phase 322 to decay the memory of the previously acquired image. For example, three scrub cycles may be performed on the detector 112 during the acceleration/deceleration phase 322.

The control returns to Step 412, and the Steps 412 through 420 are repeated for every image that has been entered into the application. If, at Step 414, no other tomographic image is prescribed, then control passes to Step 422.

At Step 422, the process is similar to Step 418. The x-ray tube 102 and the detector 112 have completed their respective travel distances Xot(cm) 316 and Xdet (cm) 318. The x-ray tube 102 stops emitting x-rays, decelerates according to the deceleration profile, and stops moving. The raw data acquired by detector 112 is read out by the image processor 120 while the detector 112 is decelerating. The image processor 120 may correct the raw data, as stated previously, before storing the data in the image storage device 124. The image is immediately displayed on the monitor 122 in a multi-image format display pattern, together with any previously acquired images of the same study. The images can be immediately evaluated without having to develop the images on film or from a CR plate.

While the invention has been described with reference to at least one embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for acquiring digital x-ray images, said method comprising:

identifying scan parameters designating slices of interest from a patient anatomy;

calculating scan ranges for each of said slices, said scan images corresponding to distances traveled by each of a detector and x-ray tube while said x-ray tube exposes said detector to radiation;

calculating first and second preparation positions for each of said x-ray tube and detector, said first and second preparation positions being located at opposite ends of said scan ranges and corresponding to a distance traveled by said x-ray tube and detector, said x-ray tube not exposing said detector to x-rays while moving through said preparation positions;

moving said detector and x-ray tube to said first detector and x-ray tube preparation positions, respectively;

acquiring a first x-ray image with said detector while moving said detector in a first direction over a first detector scan range and moving said x-ray tube in a second direction over a first tube scan range, said second direction differing from said first direction, said first x-ray image being acquired based on said scan parameters;

moving said detector and x-ray tube to said second detector and x-ray tube preparation positions, respectively;

positioning said detector and x-ray tube at said second detector and x-ray tube preparation positions, respectively, after said acquiring a first x-ray image step; and acquiring a second x-ray image with said detector while moving said detector in said second direction over a second detector scan range and moving said x-ray tube in said first direction over a second tube scan range, said second x-ray image being acquired based on said scan parameters.

2. The method of claim 1, wherein the scan parameters include at least one of: a focal plane of interest; a sweep angle; a focal plane thickness; and an exposure time.

3. The method of claim 1, further comprising modifying said scan parameters before scanning a next x-ray image.

4. The method of claim 1, said calculating step further comprising:

loading stored x-ray tube angulation data and detector and x-ray tube velocity and travel distances corresponding to a subsequent x-ray image while moving said x-ray tube through said second preparation position.

5. The method of claim 1, further comprising calculating detector and x-ray tube travel distances and sweep velocities for each of said first and second detector and tube scan ranges based on said scan parameters.

6. The method of claim 1, further comprising:

displaying said first x-ray image on a monitor before completing said step of acquiring said second x-ray image; and after acquiring said second x-ray image, displaying said first and second x-ray images simultaneously on the monitor in a multi-image format.

7. The method of claim 1, further comprising:

saving said first x-ray image in an image storage device; and displaying said first x-ray image on a monitor in a multi-image format display before completing said step of acquiring said step of acquiring said second x-ray image.

* * * * *